United States Patent [19]

Catapano

[11] Patent Number: 4,711,876

[45] Date of Patent: Dec. 8, 1987

[54] PROCESS FOR THE TREATMENT AND REMISSION OF AIDS (ACQUIRED IMMUNE DEFICIENCY SYNDROME)

[76] Inventor: Salvatore J. Catapano, 66 S. Brush Dr., Valley Stream, N.Y. 11581

[21] Appl. No.: 804,858

[22] Filed: Dec. 5, 1985

[51] Int. Cl.$^4$ ...................... A61K 39/00; A61K 39/02
[52] U.S. Cl. ........................................ 514/2; 514/885; 424/92
[58] Field of Search ................. 424/92, 58; 514/2, 21, 514/885; 128/154; 530/820, 825

[56] References Cited

U.S. PATENT DOCUMENTS 4,385,068  5/1983  Kendall et al. ...................... 424/85
4,439,199  3/1984  Amkraut et al. ..................... 530/351

Primary Examiner—Delbert R. Phillips
Assistant Examiner—Nathan M. Nutter
Attorney, Agent, or Firm—Roylance, Abrams, Berdo & Goodman

[57] ABSTRACT

A method for treating a human patient to effect the remission of AIDS, which comprises parenterally administering to the AIDS patient typhoid vaccine in a therapeutically effective amount which is sufficient to provide immunostimulating activity.

6 Claims, No Drawings

PROCESS FOR THE TREATMENT AND REMISSION OF AIDS (ACQUIRED IMMUNE DEFICIENCY SYNDROME)

BACKGROUND OF THE INVENTION

This invention relates to a process with an FDA approved adjuvant which is non-toxic to bring about the stimulation of leukocytes which inactivate the AIDS condition.

Currently, there are no drugs available anywhere that have been shown to cure AIDS, although the search for such drugs is being pursued vigorously. Some drugs have been found that inhibit the action of HTLV-III, but these do not lead to clinical improvement.

A test performed by the Public Health Service, National Institutes of Health, National Cancer Institute, Bethesda, Md., on typhoid vaccine is reported in a May 12, 1976 letter from Dr. Michael A. Chirigos to Dr. John Douros as follows:

"We have completed our initial experimental testing of typhoid vaccine for immunostimulating activity. The test system we used was a homograft tumor response. This is similar to a skin graft where if the skin graft is not compatible to the host, the host will reject it by an immunological response. The immune cells involved in the immunological response are T-Lymphocyte macrophages or B-Lymphocytes. Our results show that typhoid vaccine stimulates macrophages. The stimulation evoked by typhoid vaccine was as good or better than the immune-stimulator we use for control. The results...[indicate]that it has capacity to stimulate macrophage cell activity (emphasis applicant's)."

"T" Lymphocytes are responsible for cellular immunity. "B" Lymphocytes are responsible for humoral immunity. Two basic, but closely allied, types of immunity occur in the body. In one of these, the body develops circulating antibodies, which are globulin molecules that are capable of attacking the invading agent. This type of immunity is called "Humoral Immunity". The second type of immunity is achieved through the formation of large numbers of highly specialized lymphocytes that are specifically sensitized against the foreign agent. These sensitized lymphocytes have the special capability to attach to the foreign agent and to destroy it. This type of immunity is called cellular immunity or, sometimes, lymphocytic immunity.

Typhoid vaccine is antigenic. Furthermore, the process of antigenicity probably depends upon regularly recurring prosthetic radicals on the surface of the large molecule, which perhaps explains why proteins and many polysaccharides are antigenic, for they both have this characteristic.

Though most of the lymphocytes in the normal lymphoid tissue look alike when studied under the microscope, these cells are distinctly divided into two separate populations. One of the populations is responsible for forming the sensitized lymphocytes that provide cellular immunity and the other for forming the antibodies that provide humoral immunity. Both of these types of lymphocytes are derived originally in the embryo from lymphocytic stem cells in the bone marrow. The descendants of the stem cells eventually migrate to the lymphoid tissue. Before doing so, however, those lymphocytes that are eventually destined to form sensitized lymphocytes first migrate to and are preprocessed in the thymus gland, for which reason they are called "T" lymphocytes. These are responsible for cellular immunity. The other population of lymphocytes, those that are destined to form antibodies, is processed in some unknown area of the body, possibly the liver and spleen. For this reason, this population of lymphocytes is called the "B" lymphocytes, and they are responsible for humoral immunity.

SUMMARY OF THE INVENTION

In accordance with this invention, there is provided a process in which typhoid vaccine is used by itself and not in conjunction with any other treatment, including radiation therapy or chemotherapy, for the immunization and remission of AIDS. The typhoid vaccine is administered parenterally in an amount of from 0.75 to 10 c.c.

Typhoid vaccine is marketed by Wyeth Laboratories. Each c.c. contains not more than 1,000 million Salmonella Typhosa (Ty-2 strain) organisms, killed and suspended in buffered sodium chloride injection. The preservative is 0.5% phenol. It is described at page 1688, Physicians' Desk Reference, Medical Economics Company (1976).

DETAILED DESCRIPTION OF THE INVENTION

It has been found that a complete immunization and remission of a person afflicted with AIDS, may be achieved by the parenteral administration with typhoid vaccine in a concentration between 0.75 to 10 c.c. with no observed toxicity. The typhoid vaccine stimulates the formation of leukocytes which inactivate the AIDS virus. This procedure stimulates not only humoral immune response but also the reticuloendothelial system body defense mechanisms within the host so that it is capable of combatting AIDS within its body.

Since one object of this invention is to enhance the immune response of the body to combat AIDS, any other treatment, such as chemotherapy and radiation therapy which would reduce the immune response of the body, should be discontinued.

In treating for the remission of AIDS, a thorough medical history of the patient should be obtained and the patient should be given a complete physical examination. If there is evidence of the existence of pneumocystis carinii pneumonia (PCP), an infection of the lungs which has symptoms similar to other forms of pneumonia; and/or a rare type of cancer known as Kaposi's sarcoma (KS) which usually occurs anywhere on the surface of the skin or in the mouth, these should be treated. In early stages, KS may look like a bruise or blue-violet or brownish spot. The spot or spots persist, and may grow larger. KS may spread to or appear in other organs of the body. X-rays of the affected areas should be taken. The patients's temperature should be taken just prior to the administration of the typhoid vaccine. The patient should be injected with the typhoid vaccine in a quantity determined by body weight and physical condition, i.e., in the range of 0.75 to 10 c.c.

The patient must be watched closely with particular attention being given to body temperature and blood pressure. An indication that the vaccine is taking effect, is an elevation of body temperature within the range of 101°–103° F. In order to monitor the immune response of the patient, a periodic quantitative agglutination titer, e.g. a widal test, should be made. If a high agglutination titer is not obtained in ten (10) days, a second dosage of typhoid vaccine of an increased amount should be administered. The agglutination titer should be monitored until the patient shows a strong titer. Following the foregoing procedure, the patient should be allowed a rest period of three (3) to twenty-eight (28) days, or longer if necessary, to allow the enhanced body defenses to remit the AIDS condition.

While the permanent eradication of AIDS appears to be impossible, by a systematic course of injection of typhoid vaccine in accordance with the practice of this invention, the remission of AIDS will continue indefinitely or the AIDS will reach such a low level that subsequent antibiotic or chemotherapy treatments may result in 100% kill. Subsequent treatment by this process will be dependent in part on the observed response of the patient to the original dosage regimen.

To treat a patient for immunization against AIDS, the patient should be examined as previously described with respect to the remission treatment. If the patient is in generally good health, typhoid vaccine in an amount of from 0.75 to 10 c.c is administered. After three to four weeks, an agglutination or other seriological test should be performed in order to ascertain whether the patient shows a positive reaction to the vaccine. Not more than three months after injection of the vaccine, or sooner depending on the general health of the patient, an additional injection of the typhoid vaccine should be administered. This injection should be of a lesser dosage than the initial injection, being in the range of from 0.75 to 10 c.c per K.g. of body weight. Within nine months from the initial injection of the typhoid vaccine, another agglutination or seriological test should be performed to ascertain if immunization is present.

Clumping should be shown undiluted and at least 12 dilutions—from 1:2 through 1:12. Should there be an absence of immunization, the patient is again given an injection of typhoid vaccine, the amount to be determined by reference to the reaction of the patient to the prior injections.

The following examples illustrate the immunostimulating activity achieved by the practice of this invention.

EXAMPLE 1

The test system used in this example is a homograft tumor response. This is similar to a skin graft where if the skin graft is not compatible to the host, the host will reject it by immunological response. Several mice (strain CD2F1) are implanted with MBL-2 target cells from C57B1 mice. An intraperitoneal injection of typhoid vaccine ($2 \times 10^8$ organisms) is administered to each mouse seven days after tumor implantation. It is found that the implanted cells are rejected in an immunological response, the immune cells involved being T-lymphocytes, macrophages or B-lymphocytes. The test results show that the typhoid vaccine stimulates macrophages. The stimulation evoked by the typhoid vaccine is as good or better than the control immune stimulator, C. Parvum.

EXAMPLE 2

Each of a group of 10 healty mice was given an intraperitoneal injection of typhoid vaccine ($2 \times 10^8$ organisms). After seven days, each mouse in the group was inoculated with a virulent strain of mouse adenocarcinoma designated M109 ($5 \times 10^5$) tumor cells per mouse. Each of a group of 10 mice in a control group was injected with 0.2 ml. of phosphate-buffered saline and after seven (7) days was inoculated with m109 ($5 \times 10^5$ tumor cells). The survival time of the mice in the two groups was then recorded. The first mouse in the control group died 40 days following inoculation with the tumor cells, and the last mouse in this group died 62 days following inoculation with the tumor cells. In the group of mice treated with typhoid vaccine, the first mouse died 36 days following inoculation with the tumor cells and the last mouse died 65 days following inoculation with the tumor cells. The median survival time of the mice in the control group was 47.5 days and the median survival time for the mice in the group tested with typhoid vaccine was 50.0 days, or 2.5 days more than for the control group.

The following example illustrates the treatment of a patient afflicted with AIDS.

EXAMPLE 3

On day one, a patient afflicted with AIDS is examined. He is a black male, 38 years of age, weighs 150 pounds (regular weight 196–205 pounds) and is six feet, two inches tall. He complains of extreme tiredness, sometimes combined with headaches, dizziness and light-headedness. He has a continual fever and night sweats. He has suffered loss of weight amounting to more than 40 pounds, which is not due to dieting. He has swollen glands in the neck, armpits and groin. He bruises more easily than usual and has progressive shortness of breath. He also has a heavy, continual dry cough, although he does not smoke, which has lasted too long to be a cold or flu. A thick, whitish coating on his tongue is accompanied by a sore throat. The patient is very weak and tired and has a temperature of 102° F. The patient is given a complete examination and tested to determine if he is allergic to typhoid vaccine. It is determined that he is not allergic. The patient is treated by the parenteral administration of 0.75 c.c. of typhoid vaccine. The patient is advised to remain for three hours and then to leave.

On day eight, the patient is again examined. His headaches, dizziness, temperature and cough are determined to be diminished. After another examination, tests, and evaluation, the patient is given 1.0 c.c. of typhoid vaccine and advised to return a week later.

On day 15, the patient is again examined. He advises that his headaches and dizziness are gone. His condition is much improved. After another examination, he is given 0.75 c.c. of typhoid vaccine and advised to return a week later.

On day 22, the patient is again examined and it is found that the swollen glands in the neck, armpits and groin have reduced in size. He advises that the night sweats are gone. He is given another 0.75 c.c. injection of typhoid vaccine and advised to return a week later.

On day 29, the patient is again examined. He appears to be controlled. He is now asymptomatic. The patient informs that his eating is much improved and that he has gained five pounds. He reports no aches, sore throat, dizziness, fever, cough, and the swollen glands are much reduced. He is given another injection of 0.75 c.c. of typhoid vaccine. At this time, it is concluded that his affliction is in a state of remission.

What is claimed is:

1. A method of treating a human patient to effect the remission of symptoms associated with AIDS, which comprises parenterally administering, in multiple injections, to the patient in need of such treatment typhoid vaccine in a therapeutically effective amount which is sufficient to provide immunostimulating activity.

2. The method of claim 1 wherein at least one subsequent administration occurs between 3 and 28 days after the first administration.

3. The method of claim 1, wherein more than one subsequent administration of typhoid vaccine is given, with at least one of the subsequent administrations occurring between 3 and 28 days after a previous administration.

4. A method of treating a human patient to effect the remission of symptoms associated with AIDS, which comprises parenterally administering, in multiple injections, to said patient in need of such treatment typhoid vaccine in an amount sufficient to produce substantial clumping when evaluated in an agglutination test.

5. The method as defined in claim 4 wherein the immune response of the patient is monitored by an agglutination test, and if the agglutination titer is not strong, additional typhoid vaccine is administered.

6. The method as defined in claim 3 wherein the administration of typhoid vaccine in repeated until the agglutination test indicates substantial clumping.

* * * * *